United States Patent
Fernendes et al.

(10) Patent No.: US 6,997,710 B2
(45) Date of Patent: Feb. 14, 2006

(54) DENTAL PROSTHESIS POST AND CORE ASSEMBLY

(76) Inventors: Americo Fernendes, # Carmarthen Blvd., Winnipeg, Manitoba (CA) 43P 0W3; Gordon D. Blacklock, 3321 Columbia, NE, Albuquerque, NM (US) 87107

( * ) Notice: Subject to any disclaimer, the term of this patent is extended or adjusted under 35 U.S.C. 154(b) by 2 days.

(21) Appl. No.: 10/206,328

(22) Filed: Jul. 29, 2002

(65) Prior Publication Data

US 2004/0018470 A1    Jan. 29, 2004

(51) Int. Cl.
*A61C 8/00*    (2006.01)
(52) U.S. Cl. ..................................... 433/173
(58) Field of Classification Search ................ 433/172, 433/173, 174, 175, 176, 201.1
See application file for complete search history.

(56) References Cited

U.S. PATENT DOCUMENTS

| | | | | |
|---|---|---|---|---|
| 4,975,059 A | * | 12/1990 | Sendax | 433/173 |
| 5,030,095 A | * | 7/1991 | Niznick | 433/173 |
| 5,073,110 A | | 12/1991 | Barbone | 433/173 |
| 5,316,477 A | | 5/1994 | Calderon | 433/173 |
| 5,350,301 A | | 9/1994 | De Buck | 433/173 |
| 5,350,302 A | | 9/1994 | Martin | 433/174 |
| 5,839,898 A | * | 11/1998 | Fernandes | 433/173 |
| 5,863,200 A | * | 1/1999 | Hamada et al. | 433/173 |
| 6,500,003 B1 | * | 12/2002 | Nichinonni | 433/173 |
| 6,527,553 B1 | * | 3/2003 | Yeung | 433/173 |

* cited by examiner

*Primary Examiner*—John J Wilson
(74) *Attorney, Agent, or Firm*—Siemens Patent Services, LC

(57) ABSTRACT

A novel post and core assembly for the implantation of a dental prosthesis is set forth in the present invention. Comprised of separate post and core elements of a laser weldable material, the assembly allows for an infinite number of precise lengths and angular deviation between the post and core to precisely align a prosthesis with existing teeth/prostheses without delays in fabrication outside of the dentist's office, as is typically required in prior art assemblies. The post and/or core may be cut to the desired length and angle and welded, on site, with a minimal requirement for fabrication equipment.

5 Claims, 4 Drawing Sheets

DENTAL PROSTHESIS POST AND CORE ASSEMBLY

This application is related to U.S. Pat. No. 5,695,334, issued to Gordon D. Blacklock, et al., on Dec. 9, 1997 and U.S. Pat. No. 5,839,898, issued to Americo Fernandes on Nov. 24, 1998, included herein by reference.

BACKGROUND OF THE INVENTION

1. Field of the Invention

The present invention relates to a post and core assembly for dental implants. More particularly, the post and core assembly is constructed such that the post and core may be welded together, by a method such as laser welding, at an appropriate angle to compensate for any misalignment of the anchor which receives the post and core assembly.

2. Description of the Prior Art

When a dental prosthesis is to be attached to a patient's jaw it must be properly aligned with the other teeth or prostheses so as to be parallel thereto. A problem arises when an anchor receiving the post and core is inserted into the jaw at an angle not suitable for proper alignment. This may occur because bone tissue capable of securely supporting the anchor is not advantageously situated for appropriate placement of the anchor, or because it is simply too difficult to install properly in the available space.

An example of the former approach incorporating a rotatably adjustable post and core assembly is shown in U.S. Pat. No. 5,316,477, issued to Luis O. Calderon on May 31, 1994. Calderon's post and core must have an anchor having a circular hole for receiving the core. By contrast, the present invention has a conventional hexagonal core which cooperates with a conventional anchor having a hexagonal hole. Also, the degree of tilt, or deviation from the axis of the post and core, is adjustable in the present invention.

An example of the latter compensating approach incorporating a rotatably adjustable post and core assembly employing reference marks is shown in U.S. Pat. No. 5,350,301, issued to Vincent De Buck on Sep. 27, 1994. The post and core are provided as two separate, subsequently united structures in this invention. By contrast with the present invention, no part is deflectable into the desired position in the De Buck invention. Rather, in the De Buck device, an assembly incorporating a desired angle must be built up from individual components.

An even more complicated built up post and core assembly is described in U.S. Pat. No. 5,350,302, issued to Gerald M. Martin on Sep. 27, 1994. Some of the components of the post and core assembly have screw bores and mounting cavities which are misaligned, so that the component can be screwed to a supporting component. A subsequently mounted member continues at an angle to the supporting component. The various components allow for progressive adjustment to suit conditions as successive components are assembled and oriented at new angles to their predecessors.

U.S. Pat. No. 5,073,110, issued to Noram K. Barbone on Dec. 17, 1991, illustrates a post and core assembly wherein the post comprises the ball of a ball and socket joint. The anchor provides the socket. Unlike the present invention, which employs a conventional hexagonal core compatible with a conventional anchor having a hexagonal hole, the anchor of the Barbone device is configured to receive a ball. The Barbone anchor must be designed from the outset to cooperate with its associated post and core. Unlike the present invention, Barbone's apparatus is not deflectable.

None of the above inventions and patents, taken either singly or in combination, is seen to describe the instant invention as claimed.

SUMMARY OF THE INVENTION

The present invention provides a post and core assembly which both cooperates with a conventional anchor having an anti-rotational socket for receiving the core, and also adjusts to correct for angular misalignment of the prosthesis.

The post and core are each formed of a laser weldable material, such as titanium, or other metal. After implantation of the anchor, measurements are taken to determine the proper length and angle of deflection required to align the prosthesis with the adjoining teeth or prostheses. The mating ends of the post and core are then cut at the proper lengths and angles and bonded by welding prior to insertion into the anchor and prosthesis.

The novel post and core assembly is compatible with conventional anchors and prostheses, and therefore, does not require fabrication of special anchors and prostheses.

Accordingly, it is a principal object of the invention to provide a post and core assembly which may be variably aligned to allow the associated prosthesis to be correctly aligned with adjacent teeth or prostheses.

It is another object of the invention to provide a post and core assembly which may be used with a conventional prosthetic anchor.

It is a further object of the invention to provide a post and core assembly which is relatively easy to fabricate and install.

Still another object of the invention is to provide a post and core assembly which is economical to use.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
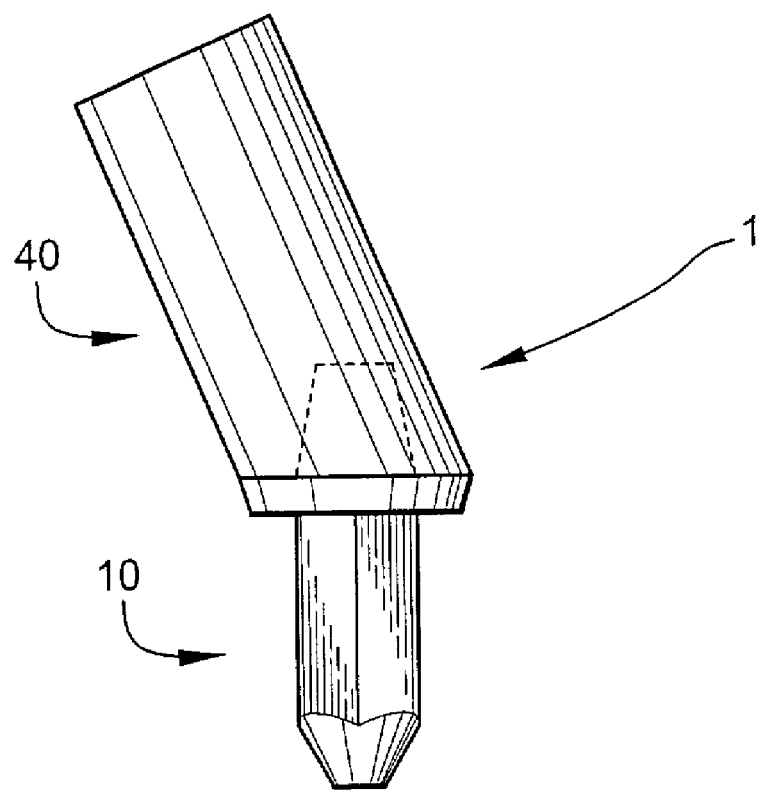
FIG. 1 is a perspective view of the joined post and core of present invention.
Figure 2:
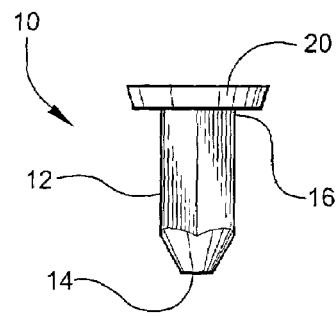
FIG. 2 is a side view of a preferred embodiment of the post of the present invention.
Figure 3:
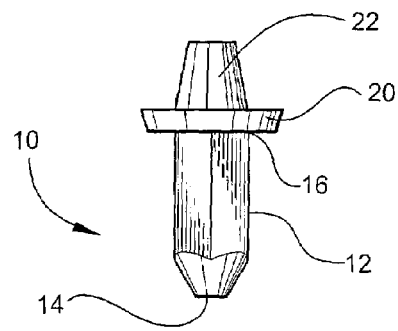
FIG. 3 is a side view of a second embodiment of the post of the present invention having a frustoconical core connector.
Figure 4:
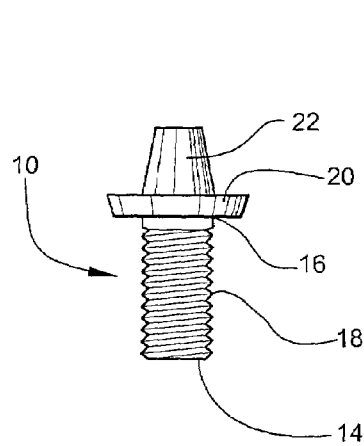
FIG. 4 is a side view of a third embodiment of the post of the present invention having a threaded post.
Figure 5:
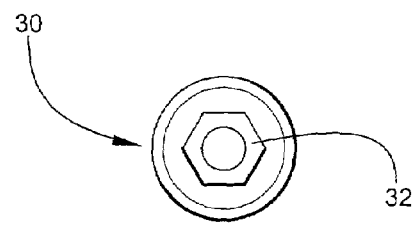
FIG. 5 is a top plan view of a typical dental implant anchor.
Figure 6:
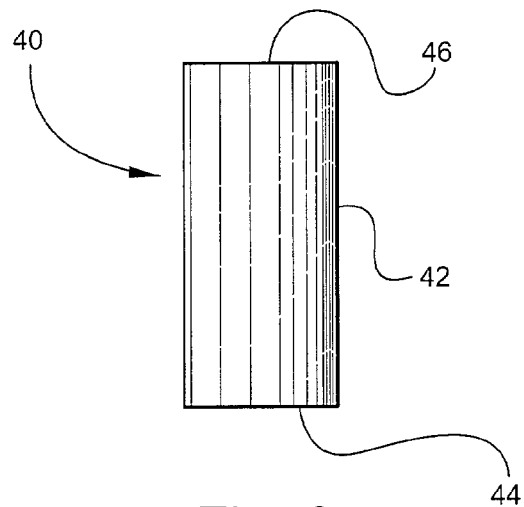
FIG. 6 is a side view of a simple core of the present invention.
Figure 7:
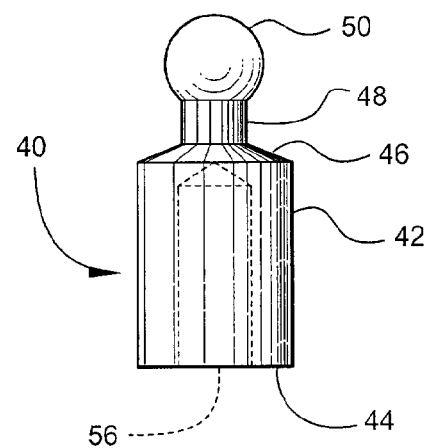
FIG. 7 is a side view of a preferred embodiment of the core of the present invention having a spherical prosthesis connector and an internal bore adapted to cooperate with the frustoconical core connector of FIG. 3.
Figure 8:
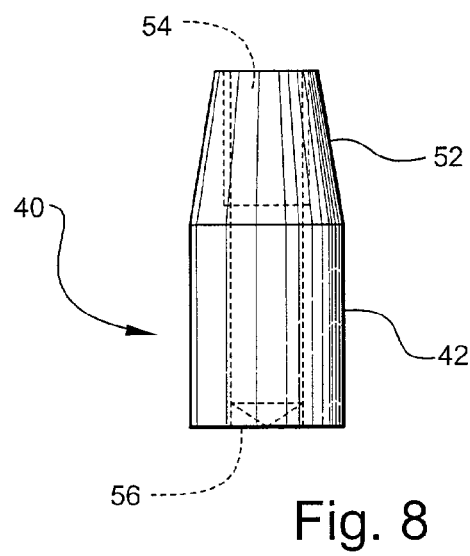
FIG. 8 is a side view of a second preferred embodiment of the core of the present invention having an internal bore adapted to cooperate with the frustoconical core connector of FIG. 3 and an internal bore for receiving an installation extension of a dental prothesis.
Figure 9:
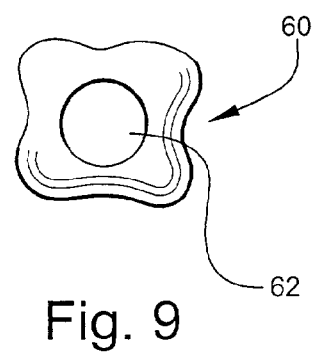
FIG. 9 is a bottom plan view of a typical dental prosthesis.

The novel post 10 and core 40 assembly 1 (FIG. 1) of the present invention is composed of a post 10 (FIGS. 2 thru 4), adapted for internally mating with a standard dental implant anchor 30 (FIG. 5), and a core 40 (FIGS. 6 thru 8), adapted for internally mating with a dental prosthesis 60 (FIG. 9). Neither anchor 30 nor prosthesis 60 are deemed to be an integral part of the present invention, but will be referenced for the purpose of disclosure.

Both post 10 and core 40 are formed of a weldable metal such as, but not necessarily limited to, titanium, gold, or a silver-palladium alloy, as are commonly used in dental practice. It would be evident to one skilled in the art that other materials could be used with equal effectiveness, so long as the material used is weldable, permanent, and stable in an oral environment (i.e., does not degrade and is not toxic when placed in the mouth).

Post 10 has a post body 12 having an axial length, a first end 14, adapted for mating internally with the cavity 32 of an anchor 30 (FIG. 5) previously imbedded within a patient's jaw, and a second end 16. In light of the fact that the cavities 32 of most anchors 30 are typically hexagonal, post body 12 is typically hexagonal in shape and dimensioned to fit snugly within the cavity 32. It would be evident to one skilled in the art, however, that post body 12 could be of any anti-rotational shape and dimensioned to fit within a cavity 32 of an anchor 30 having a shape similar to that of post body 12. Post 10 may, optionally, terminate at a blunt end (not shown) or a tapered end 14. Post body 12 may also have a substantially cylindrical shape and have threads 18 (FIG. 4) for mating with an internally threaded (not shown) cavity 32 within an anchor 30.

Post 10 may, likewise, terminate at second end 16, or may, alternatively, have a terminal platform 20 having lateral dimensions greater than those of post body 12. A terminal platform 20 facilitates the joining of a post 10 and a core 30 requiring the cutting of only the core 30, as opposed to both the post 10 and core 40 (as will be further detailed hereinbelow). Terminal platform 20 may, optionally, have a frustoconical extension 22 (FIGS. 3 & 4) extending from its center point to further facilitate alignment between the post 10 and core 40, as will be further explained hereinafter.

Like post 10, core 40 has core body 42 having an axial length, a first end 44 and a second end 46. Core body 42 may have any number of different lateral profiles, although round is preferable and, for the purposes of disclosure, will be described hereinbelow. While core body 42 may be as simple as a cylindrical or polygonal shaft (FIG. 6), a number of alternative embodiments are presented hereinbelow.

In a first embodiment (FIG. 7), core 40 has a substantially cylindrical core body 42 having a substantially planar first end 44 and a second end 46. Second end 46 may be either substantially planar or substantially frustoconical in shape. A substantially cylindrical neck 48 extends upwardly from the plane of second end 46, whether it be planar or frustoconical, neck 48 terminating with a substantially spherical head 50. Spherical head 50 is adapted to internally engage a cavity 62 within a prosthesis 60 (FIG. 9).

In a second embodiment (FIG. 8), core 40 again has a substantially cylindrical core body 42, but in lieu of neck 48 and spherical head 50, a frustoconical head 52 is at second end 46. Frustoconical head 52 would, typically, have an interior bore 54 adapted to matingly receive a mounting post (not shown) of a prosthesis 60.

Core 40 may be produced with either a solid core body 42 or with a core body 42 having an internal bore 56, a solid core 40 being utilized with a post 10 terminating in a substantially flat second end 16 or terminal platform 20 and a core 40 with internal bore 56 being utilized with a post 10 having a frustoconical extension 22.

It would be evident to one skilled in the art that, for the sake of economy and/or convenience, core 40 could be manufactured with a spherical head 50 at one end and a frustoconical head 52 at the other, or any other configuration, with core body 42 running therebetween. In the fabrication process, to be detailed hereinbelow, the core body 42 could be cut at the appropriate length and angle, and the end not used could be disposed of or saved for use in a future application.

Figure 10:
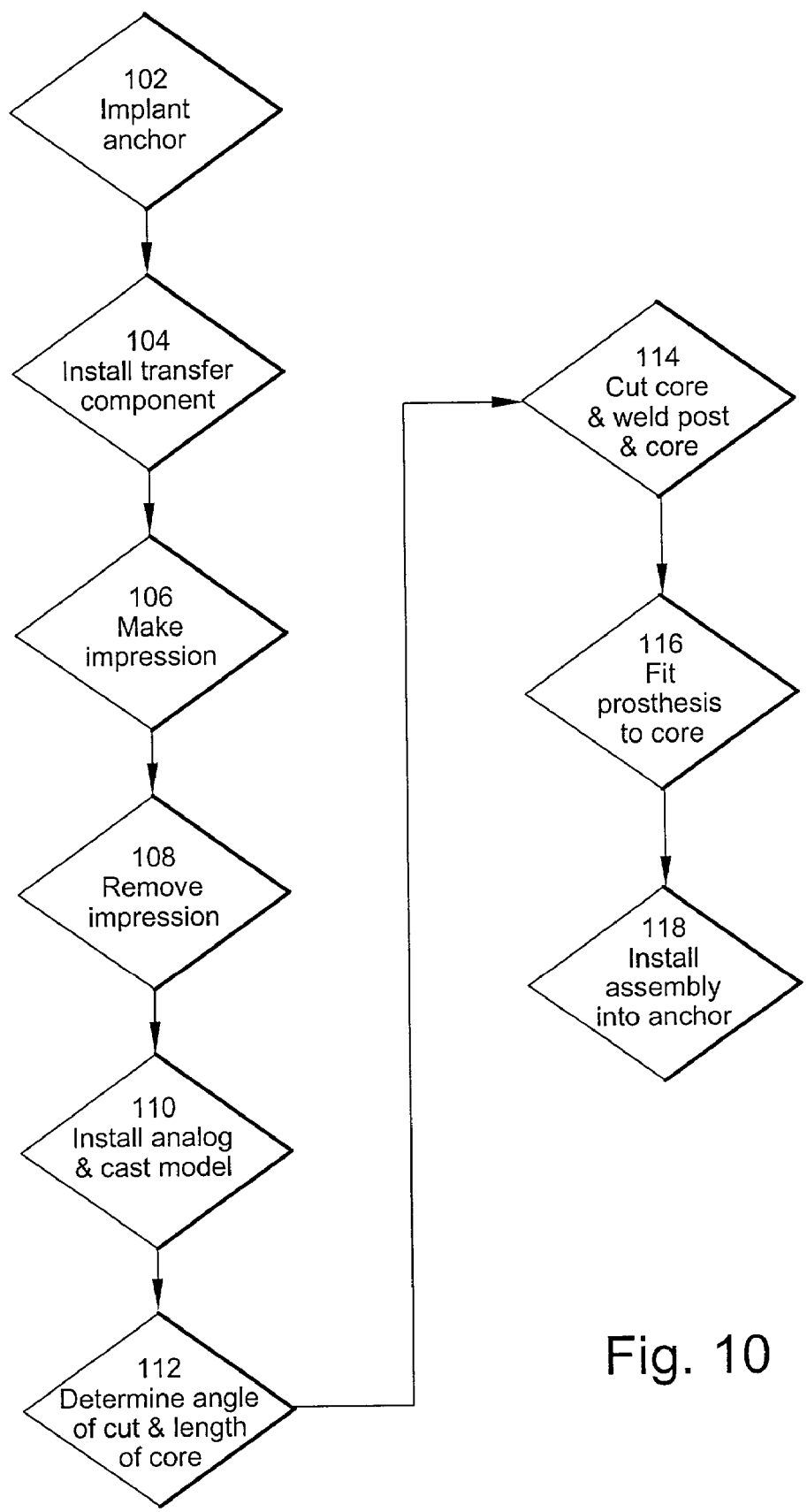
FIG. 10 is a flow chart of the method of fitting, assembling and installing the post and core assembly of the present invention.

Installation of the various embodiments of post 10 and core 40 assembly 1 is detailed at FIG. 10 and hereinbelow.

102) An anchor 30 is implanted into the jaw of a patient.

104) A transfer component (duplicate of post 10), as is commonly known in the art, is temporarily placed into the anchor.

106) An impression is made of the patient's mouth, including the anchor, transfer component and surrounding teeth or prostheses, using any one of a variety of methods commonly known in the art.

108) The impression is removed from the patient's mouth and the transfer component is re-inserted into the impression, if it failed to separate from the anchor when the impression was removed.

110) An analog (duplicate of implant 30) is placed on the transfer component and a stone (plaster of paris) model is cast, using the impression as a mold.

112) The model is used to determine the length and angle at which the core must cut.

114) A core is cut at a length and angle, as determined from the model, and fitted to the core by welding.

116) A dental crown or denture, as are known in the art, is fitted to the core.

118) The assembly is installed into the patient's mouth by securing the post into the anchor by means as are known in the art.

It is to be understood that the present invention is not limited to the embodiments described above, but encompasses any and all embodiments within the scope of the following claims.

What is claimed is:

1. A method for producing a post and core assembly for aligning a dental prosthesis within a patient's mouth and installing the same, comprising the steps of:
   utilizing a post and core assembly comprising:
   a post, said post further comprising a body having a shape which matches the shape of an implant with which said post is to be mated, an axial length and a lateral width, said post body terminating in:
   a first end adapted for internally mating with a prosthetic anchor implanted in a jaw of a patient, and a second end, said second end further comprising a terminal platform, said terminal platform for joining said post with a core; and a core, said core further comprising a body having an axial length and a lateral width, said core body further comprising:
  a first end, said first end being constructed and adapted to be joined, at a user selected length and deflection, to said second end of said post, and
  a second end, said second end being substantially cylindrical, and adaptable to internally mate with a cavity within a dental prosthesis, said post and said core being formed of at least one material from the group: titanium, gold, and a silver-palladium alloy, and said post and said core being bondable, at a user selected length and deflection, by welding, to form a single assembly; said method further comprising:

implanting a prosthetic anchor into the jaw of a patient, temporarily positioning a transfer component into the cavity within said prosthetic anchor, making an impression of said patient's mouth, including said anchor, transfer component and surrounding teeth and prostheses, removing said impression from said patient's mouth, removing said transfer component from said anchor and reinserting said transfer component into said impression, if said transfer component did not remain in said impression on removal from said mouth, placing an analog over said transfer component, casting a model of said mouth using said impression as a mold, determining the length and angle at which said core must be cut, using said model as a guide, cutting said core at said determined length and angle, bonding said post and said core by welding.

2. A method for producing a post and core assembly for aligning a dental prosthesis within a patient's mouth and installing the same, as defined in claim 1, further comprising the steps of
  fitting a prosthesis to said core, and
  securing said assembly into said implant.

3. A method for producing a post and core assembly for aligning a dental prosthesis within a patient's mouth and installing the same, as defined in claim 1, further comprising the steps of
  securing said assembly into said implant, and
  fitting a prosthesis to said core.

4. A method for producing a post and core assembly for aligning a dental prosthesis within a patient's mouth and installing the same, as defined in claim 1, wherein said prosthesis comprises a dental crown.

5. A method for producing a post and core assembly for aligning a dental prosthesis within a patient's mouth and installing the same, as defined in claim 1, wherein said prosthesis comprises a denture.

* * * * *